US008276288B1

(12) United States Patent  
Yu

(10) Patent No.: US 8,276,288 B1
(45) Date of Patent: Oct. 2, 2012

(54) PILLOW MEASUREMENT DEVICE

(76) Inventor: Chang Jun Yu, Mount Prospect, IL (US)

( * ) Notice: Subject to any disclaimer, the term of this patent is extended or adjusted under 35 U.S.C. 154(b) by 0 days.

(21) Appl. No.: 13/108,865

(22) Filed: May 16, 2011

(51) Int. Cl.
A61B 5/103 (2006.01)
(52) U.S. Cl. .......................................... 33/512; 33/464
(58) Field of Classification Search .................. 33/419, 33/427, 428, 464, 512
See application file for complete search history.

(56) References Cited

U.S. PATENT DOCUMENTS

| 1,254,197 | A | * | 1/1918 | Berriman | 33/512 |
| 1,509,703 | A | * | 9/1924 | Bourgeois | 33/427 |
| 4,380,872 | A | * | 4/1983 | Moran | 33/427 |
| 6,003,235 | A | * | 12/1999 | Chen | 33/512 |
| 6,105,269 | A | * | 8/2000 | Kondrat | 33/512 |
| 6,957,497 | B2 | * | 10/2005 | Greenawalt et al. | 33/512 |
| 2005/0150124 | A1 | * | 7/2005 | Greenawalt et al. | 33/512 |
| 2009/0320307 | A1 | * | 12/2009 | Richter | 33/512 |

* cited by examiner

Primary Examiner — G. Bradley Bennett
(74) Attorney, Agent, or Firm — Pradip K. Sahu

(57) ABSTRACT

A pillow measurement device and a method of using it are provided. Certain embodiments of the device include a first leg, a second leg, a first movable portion slidably affixed to the second leg, a means for affixing the first movable portion to the second leg, and a second movable portion. One or more of these components may have measurement indicia imprinted on them. The device can be used to measure various anatomical parts of a person, such as head width, neck width, shoulder width, cervical length and cervical depth. Measurements taken using the device may be used to custom build a pillow for a person.

11 Claims, 4 Drawing Sheets

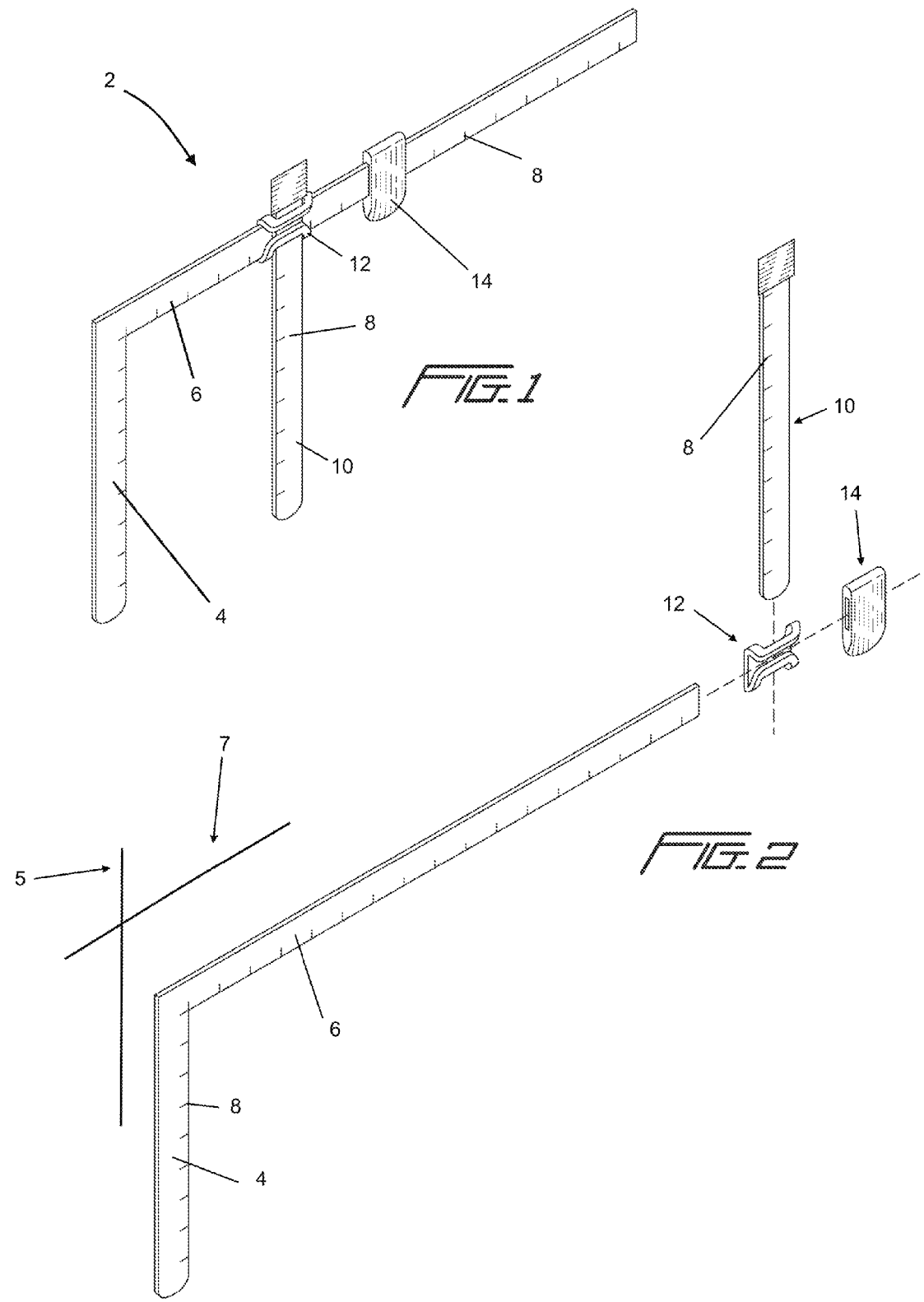

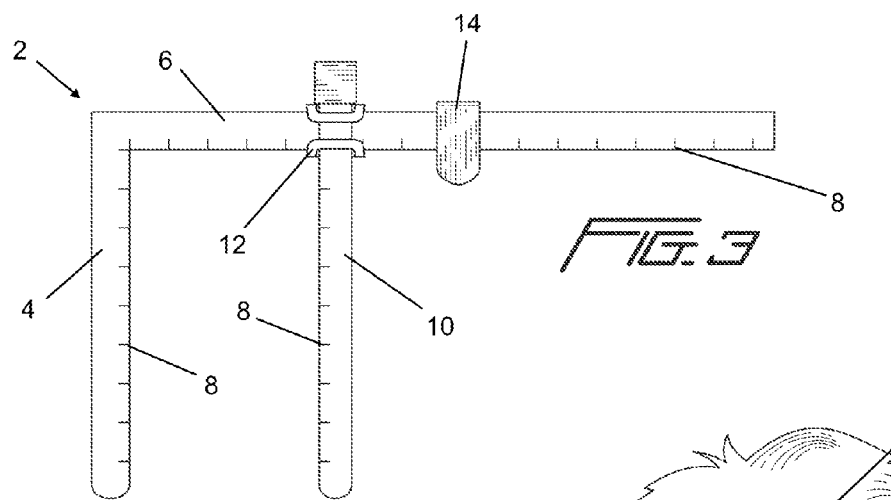
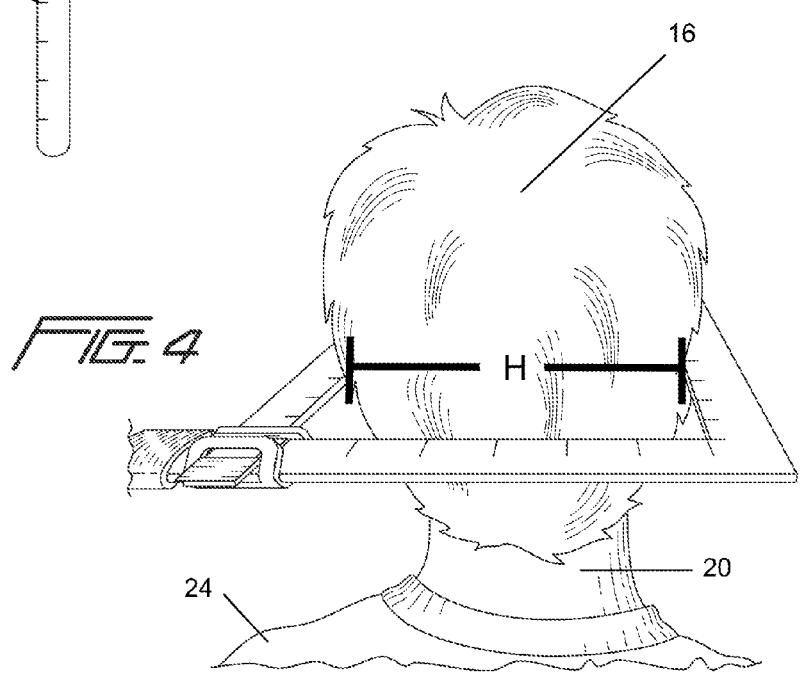
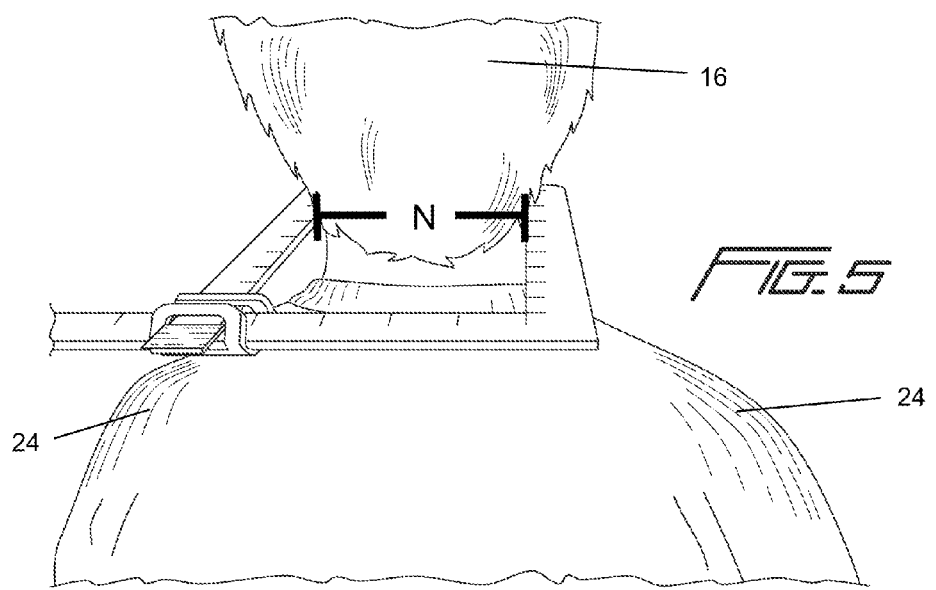

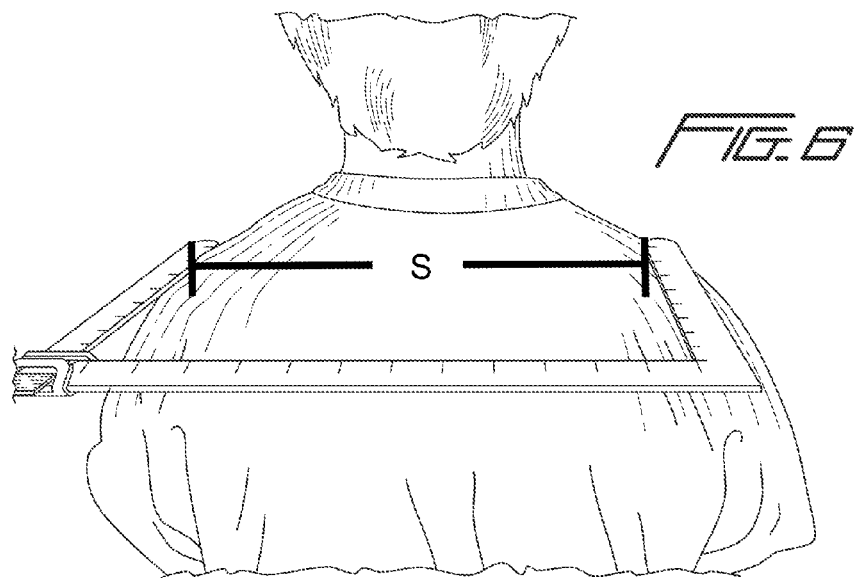
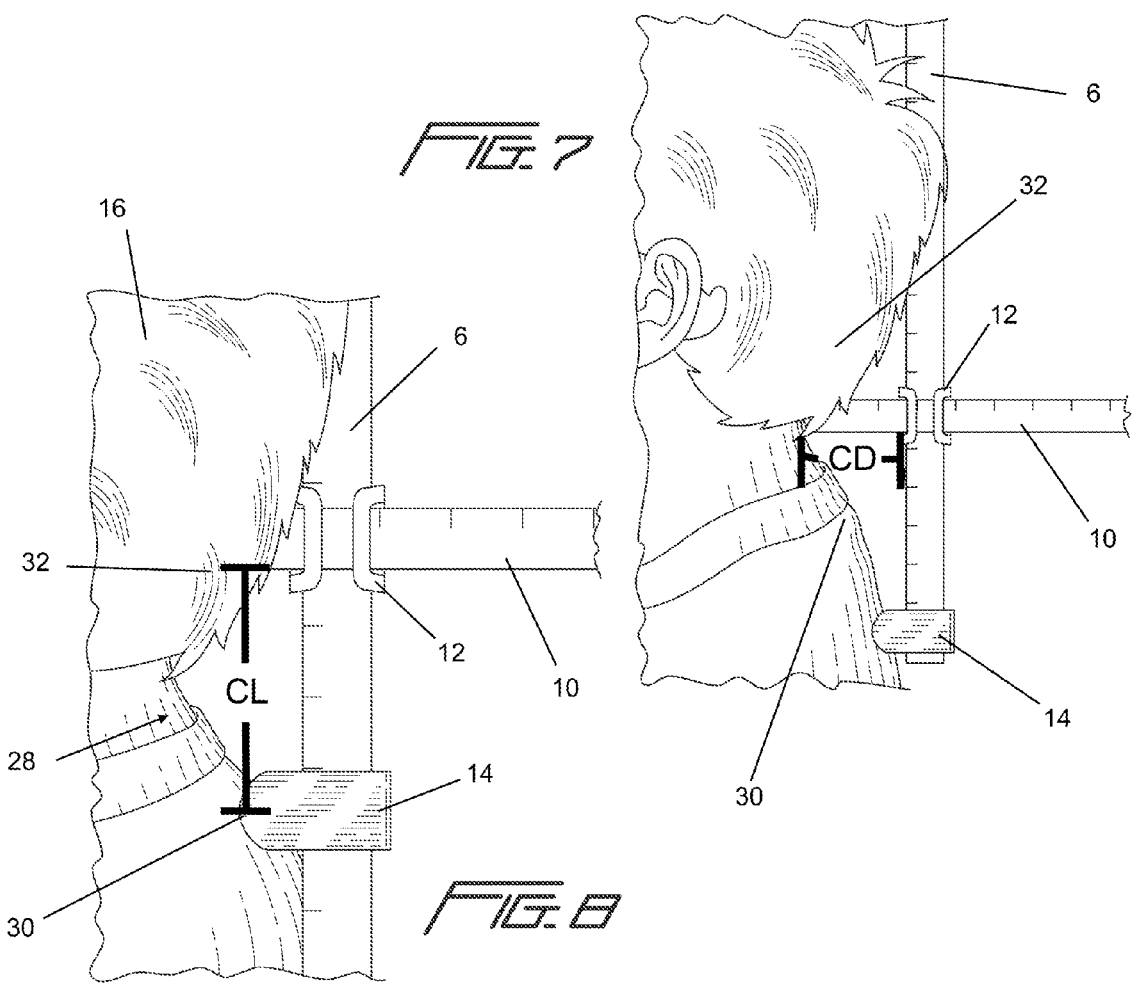

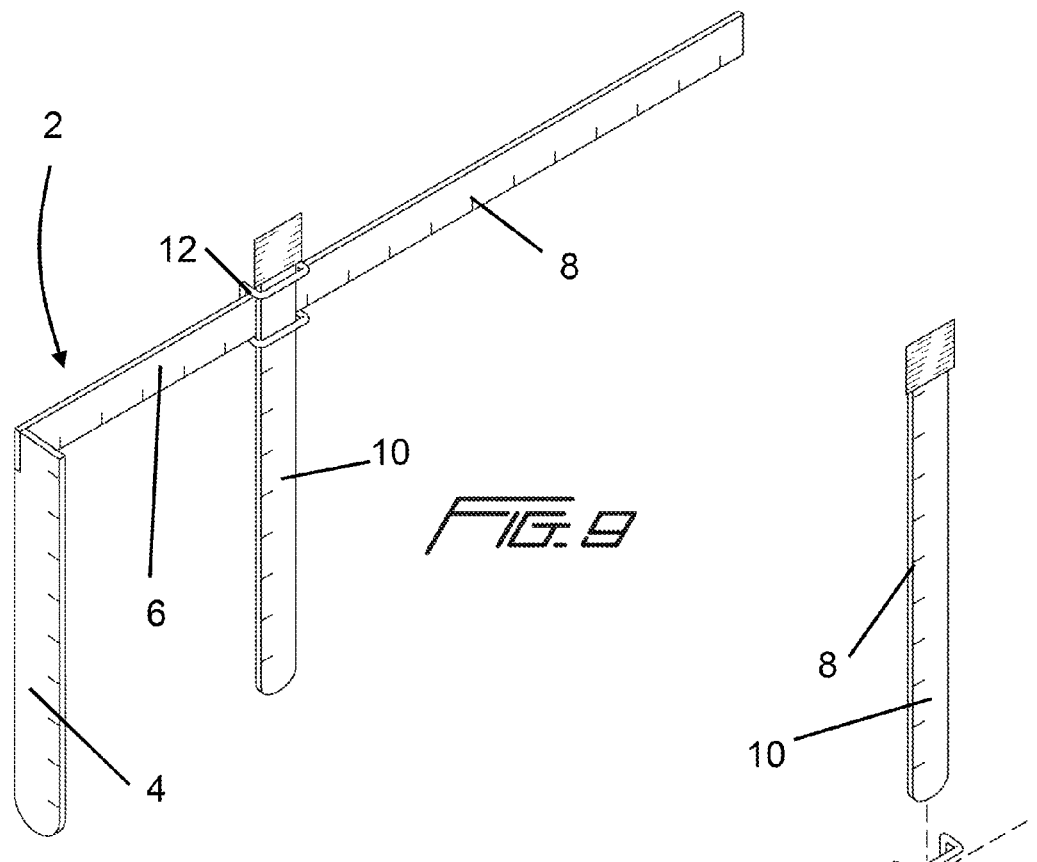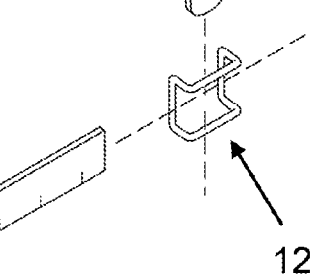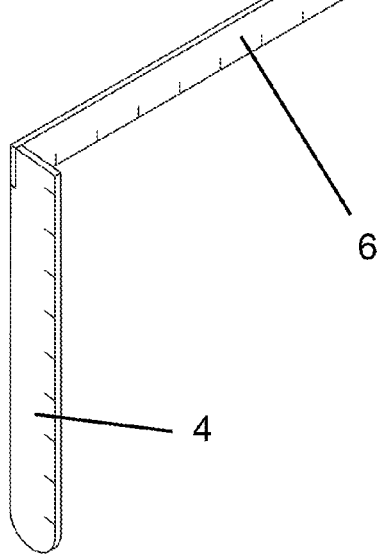

PILLOW MEASUREMENT DEVICE

BACKGROUND

Typical pillows are mass produced and designed to try to accommodate entire populations. They are designed merely to provide a cushion for people to slightly elevate their heads and necks while they are sleeping. The pillows are more or less one size fits all, and they can't be easily adjusted to conform to the unique body contour of an individual. For this reason, several companies have developed adjustable, functional therapeutic pillows. In fact, many of these therapeutic pillows can maintain a person's neck curvature and spinal alignment during sleep by using different sizes, shapes, and densities of supporting components and materials. Not only do many of these pillows have therapeutic uses, many are also comfortable. Users can try to adjust the size or shape of these pillows by, for example, inflating them or placing some type of an insert inside them. However, many of these pillows are difficult to use, and many are not very effective. More importantly, they do not always fit a person's unique body shape.

It would be desirable to have a way to measure a person's unique body shape easily so that a pillow could correspond perfectly to such shape. The measurement device and the method of using it could be used, for example, to provide therapeutic benefits to patients. Chiropractors, physiatrists, orthopedists, and physical therapists would especially find the device and method to be very useful.

BRIEF SUMMARY OF THE INVENTION

A unique measuring device is provided to accurately measure a person's spine, head, neck, shoulders and body curvature so that the measurements can be used to custom make a pillow. A method for using the measurement device is also provided. In an embodiment, the measuring device comprises an "L" shaped portion that has a first leg that is on a y-axis and a perpendicular second leg that is on an x-axis. Both legs may have measurement indicia imprinted on them. There is also a first movable portion that is slidably affixed to the "L" shaped portion so that the movable portion can be slid both parallel to the x-axis as well as parallel to the y-axis. The first movable portion may have measurement indicia imprinted on it, and it may be affixed to the "L" shaped portion by means of a resilient affixing member. There may also be a second movable portion slidably affixed to the "L" shaped portion. A user can obtain accurate measurements of a person's body shape by sliding the movable portions and noting the length measurements that are disclosed with the measurement indicia.

In a preferred embodiment, a physician may use the measurement device to measure the length of a patient's neck, width of the head, width of the neck, width of the shoulders, and the depth of the neck as described more fully herein. These measurements can be used to custom make a pillow for the patient. These and other features and advantages of the invention are described in more detail below.

BRIEF DESCRIPTION OF THE DRAWINGS

FIG. 1 shows a perspective view of an embodiment of the measurement device.

FIG. 2 is an exploded view of the device shown in FIG. 1.

FIG. 3 is a side view of the device shown in FIG. 1.

FIG. 4. depicts the measurement device shown in FIG. 1 being used to measure the width of a person's head.

FIG. 5. depicts the measurement device shown in FIG. 1 being used to measure the width of a person's neck.

FIG. 6. depicts the measurement device shown in FIG. 1 being used to measure the width of a person's shoulders.

FIG. 7. depicts the measurement device shown in FIG. 1 being used to measure the amount of curvature or "depth" of a person's neck.

FIG. 8. depicts the measurement device shown in FIG. 1 being used to measure the length of a person's neck.

FIG. 9. depicts a perspective view of another embodiment of the measurement device.

FIG. 10. shows an exploded view of the device of FIG. 9.

DETAILED DESCRIPTION OF THE PREFERRED EMBODIMENTS

Referring now to FIGS. 1 through 3 and FIGS. 9 and 10, an embodiment of the present measuring device 2 has a first leg 4 that runs parallel to a y-axis 5 and a perpendicular second leg 6 that is parallel to an x-axis 7. The first leg 4 and second leg 6 are preferably a unitary piece, but they can be made from two or more pieces affixed together. They can be made from a variety of materials, such as plastic, metal, cardboard, or foam construction board, just to name a few. The legs 4, 6 of the device 2 may have measurement indicia 8 that are more or less like markings on conventional rulers. The major and minor ticks on the ruler can have various distances between them, and they can be in metric or imperial units.

Preferred embodiments of the device 2 include a first movable portion 10 that is slidably affixed to the second leg 6 by means of a resilient affixing means 12. The first movable portion 10 can also be made from a variety of materials, but it is preferably made from the same materials as the legs 4, 6. The first movable portion 10 also may have measurement indicia 8 on it. The means 12 for affixing the movable portion 10 to the leg 6 may be constructed and arranged so that it positively engages both the first movable portion 10 and the second leg 6 in a manner so that there is enough of a biasing force to hold the first movable portion 10 in a fixed position relative to the second leg 6. The biasing force should be strong enough to fix the first movable portion's 10 position during measurement, but it should not be so strong such that a user can not slide the movable portion 10 relatively easily when desired. The affixing means 12 may be made from a variety of materials, such as metal, plastic, foam construction board, and cardboard, just like the rest of the device 2. It can also be made from a material with magnetic properties.

A user may slide the first movable portion 10 in two main directions by exerting a relatively little amount of force. It can be slid along the second leg 6 parallel to the x-axis 5 so that the device 2 can be used like a caliper to measure the thickness of a body part. The first movable portion 10 can also be slid perpendicularly to the second leg 6 along the y-axis 7 so that the device 2 can be used to measure the depth of a curvature of a body part.

The device 2 may also have a second movable portion 14 that is slidably affixed to the second leg 6. This portion 14 is preferably self biasing so that it positively engages the second leg 6. The second portion 14 preferably exerts sufficient biasing force so that it remains in a relatively fixed position on the second leg 6 until it is slid by a user. It can be made from a variety of materials, just like the affixing means 12.

Preferred embodiments of the device 2 can be used to measure various parts of a person's body so that a pillow can be custom fitted to the person. One such method includes measuring the thickness of a person's head 16 as shown in FIG. 4. The width "H" can be measured by placing the device 2 behind the person, placing the first leg 4 against the head 16 just above the right ear, and sliding the first movable portion 10 against the head 16 so that it rests just above the left ear. The user can read the measurement indicia 8 on the second leg 6 to determine the width "H."

Similarly, as shown in FIG. 5, the width "N" of the neck 20 may be measured. The first leg 4 may be placed on the right side of the middle of the neck 20, and the first movable portion 10 may be placed on the left side of the middle of the neck 20. The user can read the measurement indicia 8 on the second leg 6 to determine the width "N." The width "S" of the person's body along the shoulders 24 can be similarly measured as shown in FIG. 6. The first leg 4 is placed against the right shoulder, the first movable portion 10 is placed against the left shoulder, and the reading is taken.

The length "CL" of a person's cervical spine 28 may be measured as shown in FIG. 8. First, the second leg 6 is held perpendicular to the ground behind the person being measured. The second movable portion 14 is placed in a fixed position on the second leg 6. The device 2 is positioned so that the second movable portion 14 is placed against the spinous process of the subject's seventh cervical vertebra 30. The seventh cervical vertebra is commonly referred to as C7 in the medical field. Next, the first movable portion 10 of the device 2 is positioned so that the second leg 6 remains perpendicular to the ground while an end of the first movable portion 10 rests against the joint between the occiput and the first cervical vertebra 32, which is commonly referred to as the C0-C1 joint in the medical field. The distance "CL" between the C0-C1 joint 32 and the C7 spinous process can be measured by noting the difference in the positions of the first movable portion 10 and the second movable portion 14 using the measurement indicia 8 on the second leg 6.

The amount of cervical curvature "CD," or the depth of the neck 20, can be measured as shown in FIG. 7. First, the second leg 6 of the device 2 is positioned perpendicular to the ground. The second movable portion 14 is moved to a lower position along the second leg 6 and placed against the subject's back. The first movable portion 10 is positioned slightly higher than the second movable portion 14. The second leg 6 is then positioned so that the top part of the second leg 6 rests against the back of the subject's head 16. Next, the second movable portion 14 is slid along the y-axis in such a manner so that one end of the second movable portion 14 touches the deepest part of the subject's neck 20 along the cervical curvature. The measurement indicia 8 on the second movable portion 14 is noted, and the cervical depth "CD" is determined. All of these measurements can be noted by the physician, and a pillow can be custom manufactured for the patient accordingly.

While particular embodiments of the present device and method of using it have been described herein, it will be appreciated by those skilled in the art that changes and modifications may be made thereto without departing from the invention in its broader aspects and as set forth in the following claims.

I claim:

1. An anatomical measurement device comprising:
   an "L" shaped portion with a first leg that runs parallel to a y-axis and a second leg that runs parallel to an x-axis;
   a first movable portion slidably affixed to the second leg, the first movable portion configured to slide both along the x-axis and the y-axis;
   a second movable portion slidably engaged with the second leg and configured to slide along the x-axis;
   a resilient affixing means for slidably affixing the first movable portion to the "L" shaped portion, wherein the resilient affixing means is constructed and arranged to allow the first movable portion to slide both along the x-axis and the y-axis, and wherein the resilient affixing means is constructed and arranged to be self-biasing so that a user may slide the first movable portion along the x-axis or the y-axis or both axes without having to actuate or touch the affixing means;
   and wherein the device is capable of measuring width of a person's head, width of a person's neck, width of a person's shoulders, a person's cervical length, a person's cervical depth, a person's ear length and a person's waist width.

2. The device of claim 1 further comprising a second movable portion configured to slide along the x-axis.

3. The device of claim 2 wherein the "L" shaped portion has measurement indicia imprinted on the first leg and the second leg; and the first movable portion has measurement indicia imprinted on it.

4. The device of claim 3 wherein the device is made, at least in part, from foam board.

5. The device of claim 3 wherein the device is made, at least in part, from plastic.

6. The device of claim 3 wherein the device is made, at least in part, from metal.

7. The device of claim 3 wherein the first leg, second leg and first movable portion are made from wood and the affixing means is made from metal.

8. A method for using the device of claim 1 comprising the following steps:
   Measuring the width of a person's head by placing the first leg on a right side of the head, placing the first movable portion on a left side of the head, placing the first movable portion on a left side of the head and noting the measurement indicia on the second leg;
   Measuring the width of the person's neck by placing the first leg on a right side of the neck, placing the first movable portion on a left side of the neck and noting the measurement indicia on the second leg;
   Measuring the width of the persons shoulders by placing the first leg on an outside portion of the person's right shoulder, placing the first movable portion on an outside portion of the person's left shoulder and noting the measurement indicia on the second leg;
   Measuring the person's cervical length by position the device so that the second leg is perpendicular to the ground, placing the second movable portion on the person's C7 spinous process, placing the first movable portion on the person's C0-C1 joint, and noting the measurement indicia on the second leg;
   Measuring the person's cervical depth by positioning the device so that the second leg is perpendicular to the ground, placing the second movable portion on the person's back, placing an upper part of the second leg against the person's head, sliding the first movable portion perpendicular to the second leg so that an end of the first movable portion touches a deepest portion of the person's cervical curvature and noting the measurement indicia on the first movable portion.

9. The method of claim 8 further comprising the step of manufacturing a pillow conforming to measurements taken of the person.

10. The method of claim 8 further comprising the step of measuring the person's ear length.

11. The method of claim 8 further comprising the step of measuring the person's waist width.

* * * * *